US012676225B2

(12) United States Patent (10) Patent No.: US 12,676,225 B2
Denault et al. (45) Date of Patent: Jul. 7, 2026

(54) SYSTEM FOR MEASURING BREATH AND FOR ADAPTING BREATH EXERCISES

(71) Applicant: MOON FACTORY INC., Montreal (CA)

(72) Inventors: Anne-Marie Denault, Montreal (CA); Osman Zeki Tekelioglu, Montreal (CA); Irene Pylypenko, Montreal (CA)

(73) Assignee: MOON FACTORY INC., Verdun (CA)

( * ) Notice: Subject to any disclaimer, the term of this patent is extended or adjusted under 35 U.S.C. 154(b) by 1059 days.

(21) Appl. No.: 17/607,629

(22) PCT Filed: May 1, 2020

(86) PCT No.: PCT/CA2020/050589
§ 371 (c)(1),
(2) Date: Oct. 29, 2021

(87) PCT Pub. No.: WO2020/220142
PCT Pub. Date: Nov. 5, 2020

(65) Prior Publication Data
US 2022/0215926 A1 Jul. 7, 2022

Related U.S. Application Data

(60) Provisional application No. 62/842,019, filed on May 2, 2019.

(51) Int. Cl.
*G16H 20/30* (2018.01)
*A63B 23/18* (2006.01)
(Continued)

(52) U.S. Cl.
CPC ........... *G16H 20/30* (2018.01); *A63B 23/185* (2013.01); *A63B 24/0075* (2013.01);
(Continued)

(58) Field of Classification Search
CPC ...... G16H 20/30; G16H 50/30; A63B 23/185; A63B 24/0075; A63B 71/0622;
(Continued)

(56) References Cited

U.S. PATENT DOCUMENTS 7,850,619 B2 * 12/2010 Gavish ..................... A61B 5/74
600/534
10,542,930 B1 * 1/2020 Sanchez ............... A61B 5/4818
(Continued)

FOREIGN PATENT DOCUMENTS

JP 2018533412 11/2018

OTHER PUBLICATIONS

Europeen Search Report; EP20798208.3; Dec. 23, 2022; Laub, Christoph.
(Continued)

*Primary Examiner* — Peter S Vasat
*Assistant Examiner* — Stephen Alvesteffer
(74) *Attorney, Agent, or Firm* — DECODE LEGAL

(57) ABSTRACT
There is described a method for coaching a breathing exercise to a user using a computing device. The method provides a sequence of user instructions for the breathing exercise and determines an expected pattern of breathing intensity from the user in accordance with the sequence of user instructions. Raw audio data stream is retrieved from a microphone associated to the computing device. The raw audio data stream is processed, and breathing events are then detected. By comparing a timing of the detected breathing events with the expected pattern of breathing intensity, compliance with the breathing exercise and future exercises can be adapted within a session or over the length of a program.

11 Claims, 9 Drawing Sheets

(51) Int. Cl.

| | | |
|---|---|---|
| *A63B 24/00* | (2006.01) | |
| *A63B 71/06* | (2006.01) | |
| *G06T 13/00* | (2011.01) | |
| *G10L 25/21* | (2013.01) | |
| *G10L 25/51* | (2013.01) | |

(52) U.S. Cl.
CPC .......... *A63B 71/0622* (2013.01); *G06T 13/00* (2013.01); *G10L 25/21* (2013.01); *G10L 25/51* (2013.01); *A63B 2024/0068* (2013.01); *A63B 2024/0096* (2013.01); *A63B 2220/808* (2013.01); *A63B 2230/405* (2013.01)

(58) Field of Classification Search
CPC .... A63B 2024/0068; A63B 2024/0096; A63B 2220/808; A63B 2230/405; G06T 13/00; G10L 25/21; G10L 25/51; A61B 5/087; A61B 5/16
USPC ........................................................ 434/236
See application file for complete search history.

(56) References Cited

U.S. PATENT DOCUMENTS

| | | | | |
|---|---|---|---|---|
| 2011/0183305 | A1* | 7/2011 | Orbach .................. | G09B 19/00 |
| | | | | 434/236 |
| 2013/0331662 | A1* | 12/2013 | Stoian .................. | A61B 5/0002 |
| | | | | 600/301 |
| 2015/0126888 | A1* | 5/2015 | Patel .................... | A61B 5/0871 |
| | | | | 600/538 |
| 2016/0371998 | A1* | 12/2016 | Fazeel .................... | G16H 20/30 |
| 2017/0055878 | A1* | 3/2017 | Chon .................. | A61B 5/0816 |
| 2017/0325779 | A1* | 11/2017 | Spina .................. | A61B 5/7425 |
| 2018/0021010 | A1 | 1/2018 | Stamatopoulos et al. | |
| 2018/0318643 | A1* | 11/2018 | Klee .................. | A61M 16/026 |
| 2018/0339122 | A1 | 11/2018 | Lunz et al. | |
| 2019/0029563 | A1 | 1/2019 | Sels et al. | |
| 2019/0053769 | A1 | 2/2019 | O'Keeffe et al. | |
| 2019/0272843 | A1* | 9/2019 | Thorpe .............. | G10L 21/0232 |
| 2020/0075044 | A1* | 3/2020 | Jankowski, Jr. ........ | G10L 17/04 |

OTHER PUBLICATIONS

Lange et al., Breath: A game to motivate the compliance of postoperative breathing exercises. Virtual Rehabilitation International Conference, Haifa Israel, Jun. 29, 2009 (Jun. 29, 2009), pp. 94-97.

* cited by examiner

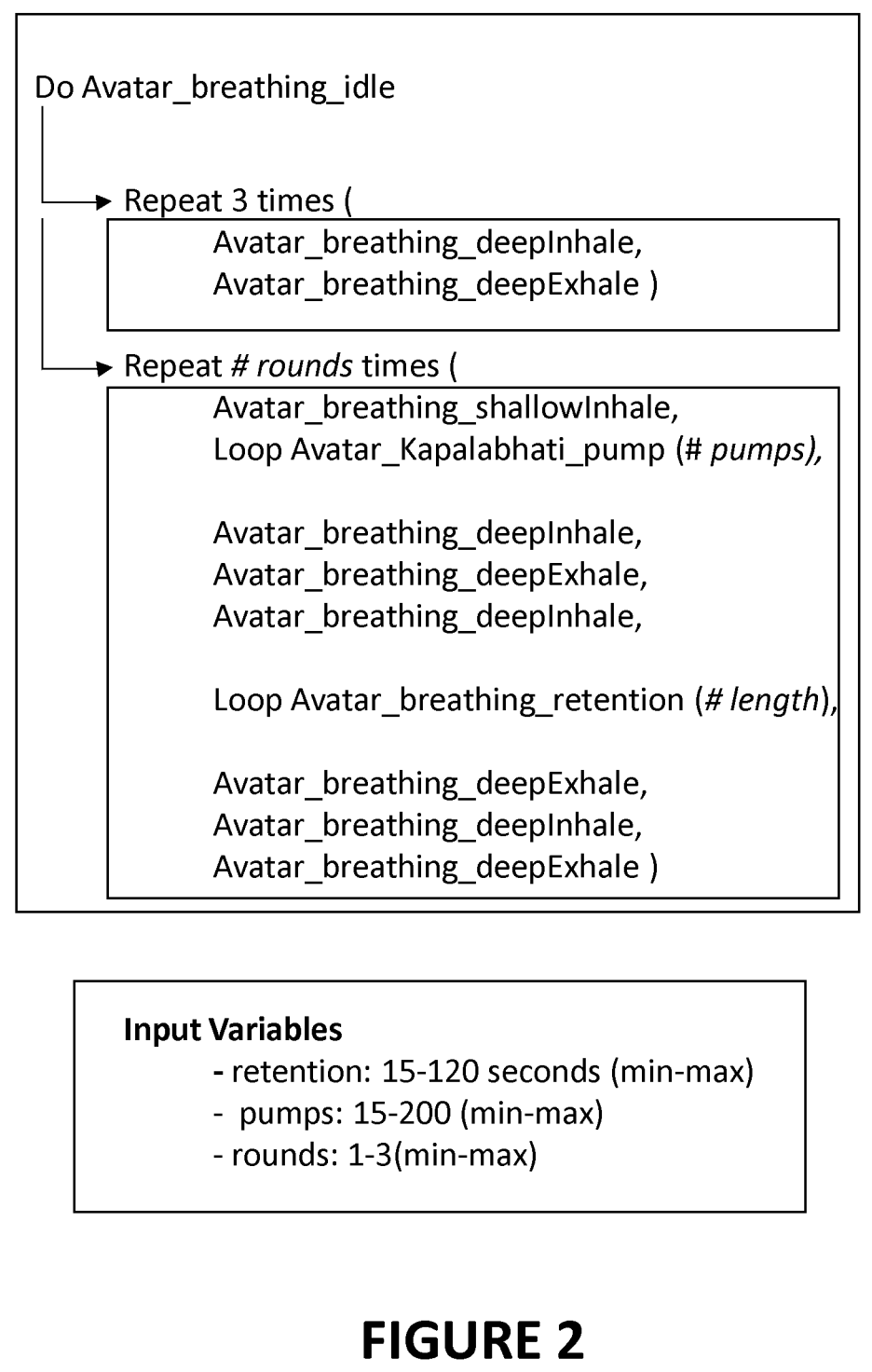

Do Avatar_breathing_idle

Repeat 3 times (
        Avatar_breathing_deepInhale,
        Avatar_breathing_deepExhale )

Repeat *# rounds* times (
        Avatar_breathing_shallowInhale,
        Loop Avatar_Kapalabhati_pump (*# pumps),*

Avatar_breathing_deepInhale,
        Avatar_breathing_deepExhale,
        Avatar_breathing_deepInhale, Loop Avatar_breathing_retention (*# length),*

Avatar_breathing_deepExhale,
        Avatar_breathing_deepInhale,
        Avatar_breathing_deepExhale )

Input Variables
      - retention: 15-120 seconds (min-max)
      - pumps: 15-200 (min-max)
      - rounds: 1-3(min-max)

FIGURE 2

Breathing Session - Time (seconds) vs Lung Capacity

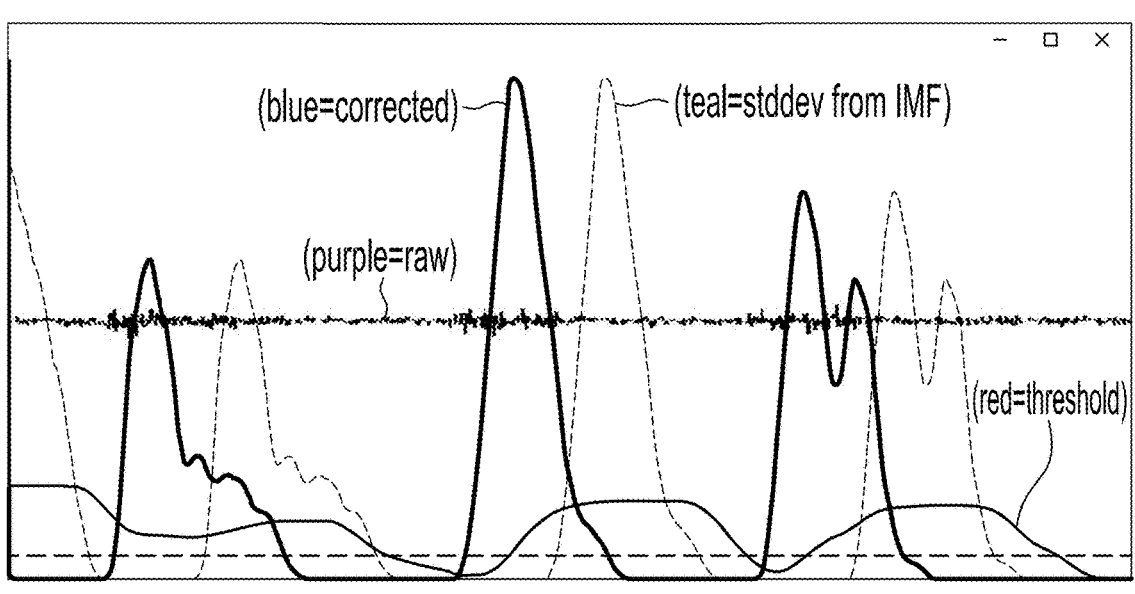
FIGURE 7
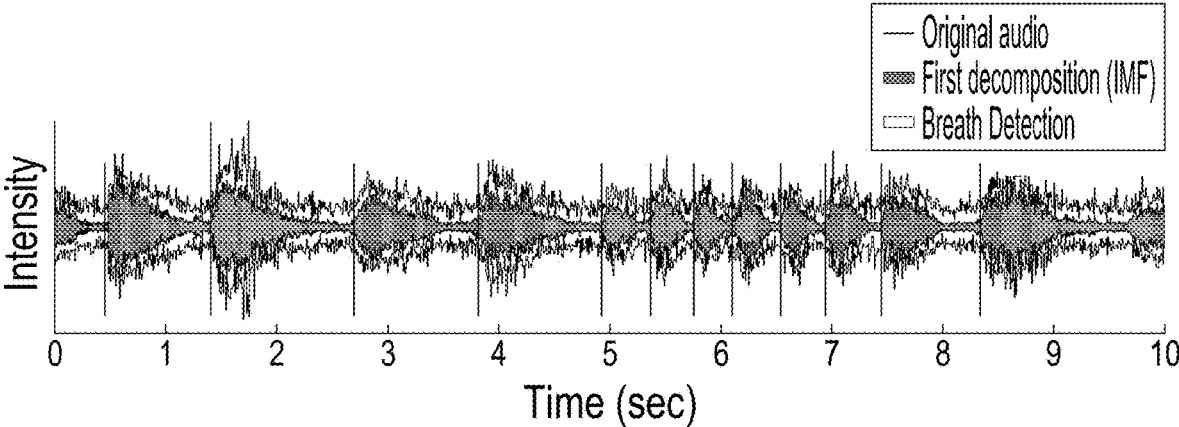
The envelope represents the outline of the IMF (orange signal)
The red line is the dynamic threshold calculated from window of 1.5 seconds (adjustable) to filer background noises.
Breath detections correspond to the cross over between the blue line and the red line.
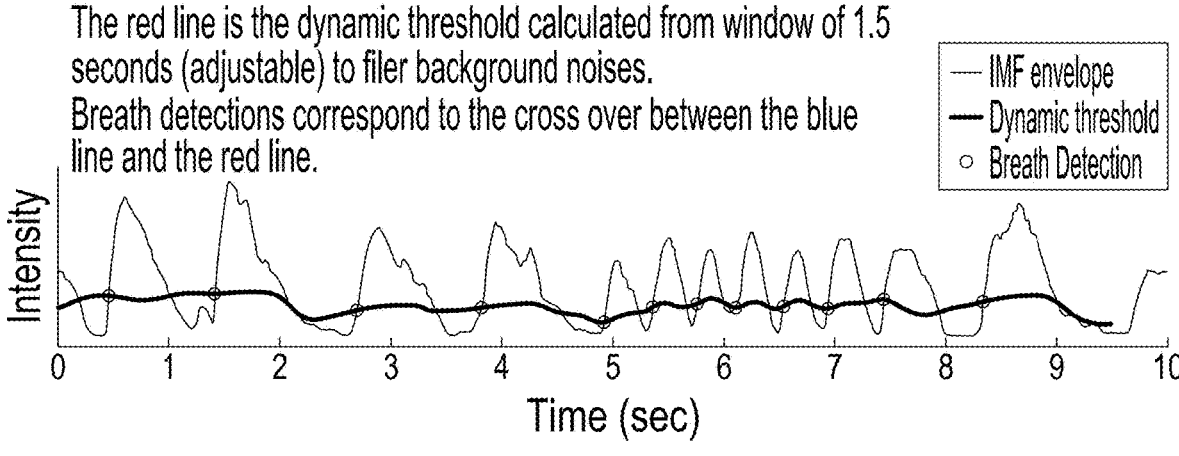
FIGURE 8

```
Initialize:

AbsoluteOffset = 0;

Executed for each audio recording:

Foreach AudioInputSample

NewSample = AudioInput // 1600 doubles at 16 000 hz
        NewImf = EMD(NewSample) // Return IMF array, same size as new sample size
        WindowIMF = [OldIMF + NewIMF]
        WindowStdDev = [...] // SAMPLESIZE
        WindowThreshold = [...] // SAMPLESIZE For (j = 0; j < SAMPLESIZE; j++)
                stddev = AvgStdDevSimplified(WindowIMF, j, SampleSize) // Modified version of standard
                deviation, more detail below
                WindowStdDev[j] = stddev;
                newThresholdValue = MovingAvg.Add(stddev * ThreasholdMultiplier);
                WindowThreshold[j] = newThresholdValue; // We smooth on 1.5s worth of record (15 samples,
                24000 doubles)
                // Beyond this point we omit signal alignment
                diff = (stddev - newThresholdValue) < 0 ? -1 : 1;
                if (diff != lastDiff) // Intersection between signal detected
                        // Intersection detected!
                        NewIntersection = [AbsoluteOffset, stddev]

IF (stdDevAdd > 0) // If the addition is positive, then we have a breath, if it's negative, we
                        have a silence
                                // New breath detected !
                                // Filter by intersection width (in seconds)
                                // Check how much the stddev peak go relative to threshold to discriminate
                        ELSE
                                // SILENCE detected LastIntersection = newIntersection
                        stdDevAdd = 0 // Reset, calculation need to be done until we get another intersection
                lastDiff = diff
                stdDevAdd += (stddev – newThresholdValue);
        AbsoluteOffset++;
        OldIMF = NewIMF
```

```
AvgStdDevSimplified:
    static double avgStdDev_Simplified(double[] buffer, int start, int count)
   {
     double output = 0;
    for (int i = start; i < start + count; i++)
    {
      double p1 = (buffer[i] - 0);
      output += p1 * p1;
    }
    return output;
   }
```

FIGURE 9

SYSTEM FOR MEASURING BREATH AND FOR ADAPTING BREATH EXERCISES

CROSS-REFERENCE TO RELATED APPLICATIONS

This application claims priority or benefit from U.S. patent application 62/842,019, filed May 2, 2019, the specification of which is hereby incorporated herein by reference in its entirety.

BACKGROUND

(a) Field

The subject matter disclosed generally relates to systems acting as a personal coach. More specifically, it relates to a system for coaching breath exercises.

(b) Related Prior Art

Yogic breathing techniques have been developed in India over thousands of years and restricted to exclusive groups, such as yogis and Hindu priests. More recently, as many ancient texts have become widely available, and eastern knowledge has spread throughout the west, more and more people are being trained in these practices. In addition, scientific research has shown the benefits of breathing exercises for many medical conditions and overall wellbeing.

There is a need to make breathing exercises available to a wider audience while ensuring that the breathing exercises are performed properly and making sure that the breathing exercises undertaken by people are at an appropriate level.

SUMMARY

In an aspect of the invention, there is provided a method for coaching a breathing exercise to a user using a computing device, the method comprising:

providing a sequence of user instructions for the breathing exercise;

determining an expected pattern of breathing intensity from the user in accordance with the sequence of user instructions;

retrieving a raw audio data stream from a microphone associated to the computing device;

from the raw audio data stream, detecting breathing events; and comparing a timing of the detected breathing events with the expected pattern of breathing intensity to determine compliance with the breathing exercise.

According to an embodiment, the computing device comprises an operating system which preprocesses the raw audio data stream from the microphone by default for access to the preprocessed raw audio data stream by any application installed on the computing device, wherein the step of retrieving the raw audio data stream comprises using OS-specific instructions directed to the operating system to avoid receiving the preprocessed raw audio data stream and retrieving the raw audio data stream, not preprocessed, directly, by preventing any alteration by the operating system on the raw audio data stream before retrieval.

According to an embodiment, the microphone comprises an associated logic module which preprocesses the raw audio data stream from the microphone by default for access to the preprocessed raw audio data stream by any application installed on the computing device, wherein the step of retrieving the raw audio data stream comprises using instructions directed to the associated logic module of the microphone to avoid receiving the preprocessed raw audio data stream and retrieving the raw audio data stream, not preprocessed, directly, by preventing any alteration by the logic module of the microphone on the raw audio data stream before retrieval.

According to an embodiment, detecting breathing events from the raw audio data stream comprises detecting that a formatted sound intensity has crossed over a threshold, wherein the threshold is based on a moving averaging window of the formatted sound intensity of a duration between 1 and 2 s.

According to an embodiment, the raw audio data stream is transformed into a formatted raw audio data stream by dividing the raw audio data stream in independently treated sample windows of a duration between 50 ms and 200 ms; and converting the raw audio data stream from 16-bit to double.

According to an embodiment, the formatted raw audio data stream is transformed into the formatted sound intensity by decomposing the formatted raw audio data stream into Intrinsic Mode Functions using Empirical Mode Decomposition.

According to an embodiment, detecting breathing events comprises:

determining the threshold for each of the sample windows based on the moving averaging window and identifying intersections of the threshold with an envelope of the Intrinsic Mode Functions;

for each of the sample windows, calculating an average standard deviation and the threshold to discriminate between a start and an end of a breath event; and recording and time-stamping each start of a breath event.

According to an embodiment, there are further provided the steps of:

based on the comparing of the timing of the detected breathing events with the expected pattern of breathing intensity to determine compliance with the breathing exercise, generating a score indicative of the compliance; and among a library of possible breathing exercises, automatically proposing a future breathing exercise with an adjusted level of difficulty which is based on a level of difficulty of the breathing exercise which was performed and on the score.

According to an embodiment, there is further provided the step of using a game engine, animating an animated character according to the expected pattern of breathing intensity in timing with the instructions, and displaying the character on the computing device.

According to an embodiment, detecting breathing events comprises integrating a formatted sound intensity over a continuous period of time covering a detected breath event to evaluate a volume of air that was inspired or expired during the detected breath event.

According to an embodiment, there is further provided the step of comparing a formatted sound intensity over a continuous period of time with the expected pattern of breathing intensity.

According to an embodiment, there is further provided the step of adapting future instructions of the breathing exercise based on the step of comparing such that if the step of comparing indicates a low compliance with the expected pattern of breathing intensity, a level of difficulty of the future instructions is lowered within a single session of the breathing exercise.

According to an embodiment, there are further provided the steps of:

using a game engine, animating an animated character according to the expected pattern of breathing intensity in timing with the instructions, and displaying the animated character on the computing device; and using the same game engine, displaying a plot of the formatted sound intensity in comparison with the expected pattern of breathing intensity over the continuous period of time simultaneously with the animated character or at an end of presentation of the animated character.

According to another aspect, there is provided a computing device for coaching a breathing exercise to a user, the computing device comprising a microphone associated thereto, a memory storing instructions and a processor executing the instructions to execute steps of:

providing a sequence of user instructions for the breathing exercise;

determining an expected pattern of breathing intensity from the user in accordance with the sequence of user instructions;

retrieving a raw audio data stream from the microphone;

from the raw audio data stream, detecting breathing events; and comparing a timing of the detected breathing events with the expected pattern of breathing intensity to determine compliance with the breathing exercise.

According to an embodiment, the computing device comprises an operating system which preprocesses the raw audio data stream from the microphone by default for access to the preprocessed raw audio data stream by any application installed on the computing device, wherein the step of retrieving the raw audio data stream comprises using OS-specific instructions directed to the operating system to avoid receiving the preprocessed raw audio data stream and retrieving the raw audio data stream, not preprocessed, directly, by preventing any alteration by the operating system on the raw audio data stream before retrieval.

According to an embodiment, detecting breathing events from the raw audio data stream comprises detecting that a formatted sound intensity has crossed over a threshold, the threshold based on a moving averaging window of the formatted sound intensity of a duration between 1 s and 2 s.

According to an embodiment, the raw audio data stream is transformed into a formatted raw audio data stream by:

dividing the raw audio data stream in independently treated sample windows of a duration between 50 ms and 200 ms; and converting the raw audio data stream from 16-bit to double.

According to an embodiment, the formatted raw audio data stream is transformed into the formatted sound intensity by decomposing the formatted raw audio data stream into Intrinsic Mode Functions using Empirical Mode Decomposition.

According to an embodiment, detecting breathing events comprises:

determining the threshold for each of the sample windows based on the moving averaging window and identifying intersections of the threshold with an envelope of the Intrinsic Mode Functions;

for each of the sample windows, calculating an average standard deviation and the threshold to discriminate between a start and an end of a breath event; and recording and time-stamping each start of a breath event.

According to an embodiment, there are further provided the steps of:

based on the comparing of the timing of the detected breathing events with the expected pattern of breathing intensity to determine compliance with the breathing exercise, generating a score indicative of the compliance; and among a library of possible breathing exercises, automatically proposing a future breathing exercise with an adjusted level of difficulty which is based on a level of difficulty of the breathing exercise which was performed and on the score.

According to an embodiment, there is further provided the step of comparing a formatted sound intensity over a continuous period of time with the expected pattern of breathing intensity.

According to an embodiment, there are further provided the steps of:

using a game engine, animating an animated character according to the expected pattern of breathing intensity in timing with the instructions, and displaying the animated character on the computing device; and using the same game engine, displaying a plot of the formatted sound intensity in comparison with the expected pattern of breathing intensity over the continuous period of time simultaneously with the animated character or at an end of presentation of the animated character.

As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description of selected embodiments, taken in combination with the appended drawings, in which:

FIG. 2 is a flowchart diagram illustrating a pseudocode generating instructions for coaching breath exercises, including repetitions and transitions between statuses, according to an embodiment;

FIG. 7 is a graph illustrating raw sound data, standard deviation of IMF, corrected standard deviation of IMF and dynamic threshold, according to an embodiment;

FIG. 8 is a graph illustrating (1) raw sound data, IMF, and breath events and (2) envelope of IMF and dynamic threshold with breath events detected on the graph, according to an embodiment;

FIG. 9 is a flowchart diagram illustrating a pseudocode generating instructions for detecting breath events in a data set transformed by EMD into IMF, according to an embodiment;

It will be noted that throughout the appended drawings, like features are identified by like reference numerals.

DETAILED DESCRIPTION

The system described herein is intended to make breathing exercises more accessible to a wider audience by using an electronic device to improve adherence of the user to the instructions of a breathing exercise, and to adapt the breathing exercise being coached to the actual breathing pattern of the user, which is being measured in real time.

To put it briefly, each breathing technique is encoded into an internal computer representation and an associated algorithm, so that each breathing exercise can be translated into instructions that are implemented and adapted into a computer system. According to an embodiment, an animated coach can read these instructions and teach them to the user, wherein the animation of the coach character on a display is adapted to the breathing exercise being instructed, and optionally further adapted to the feedback from the user, such feedback including breathing patterns from the user and compliance of the measured breathing patterns with the breathing exercise being instructed.

According to an embodiment, the whole method goes as follows. The virtual coach implemented on the electronic device is instructed to voice out loud instructions which explain the breathing exercise and guide the user through them, giving precise instructions on when and how to inhale, exhale and retain the breath, for example, in accordance with the method shown in FIG. 2, which transitions between states such as those shown in FIG. 1, with the goal of having the user breathe according to a pattern such as the one shown in FIG. 3. There are audio instructions and visual cues by the animation on the electronic device. As the user is practicing the breathing exercise, the microphone within the same electronic device (or paired therewith) is used, most probably necessitating the step of providing a direct access of the installed application to the raw audio data collected by the microphone, which can be done by accessing directly the raw audio stream within the operating system of the device. After doing so, the breath-containing audio stream is recorded and detected using a method of detection which can be illustrated with a graph is being plotted with two lines as shown in FIG. 7 or 8, where breath events are detected, to assess real-life compliance of the user with the instructions which were given by the virtual coach, in real time.

There is now described an exemplary embodiment of a method for encoding of a breathing technique, in this example, "Kapalabhati" (example only, as any other breathing exercise can be encoded).

Figure 1:
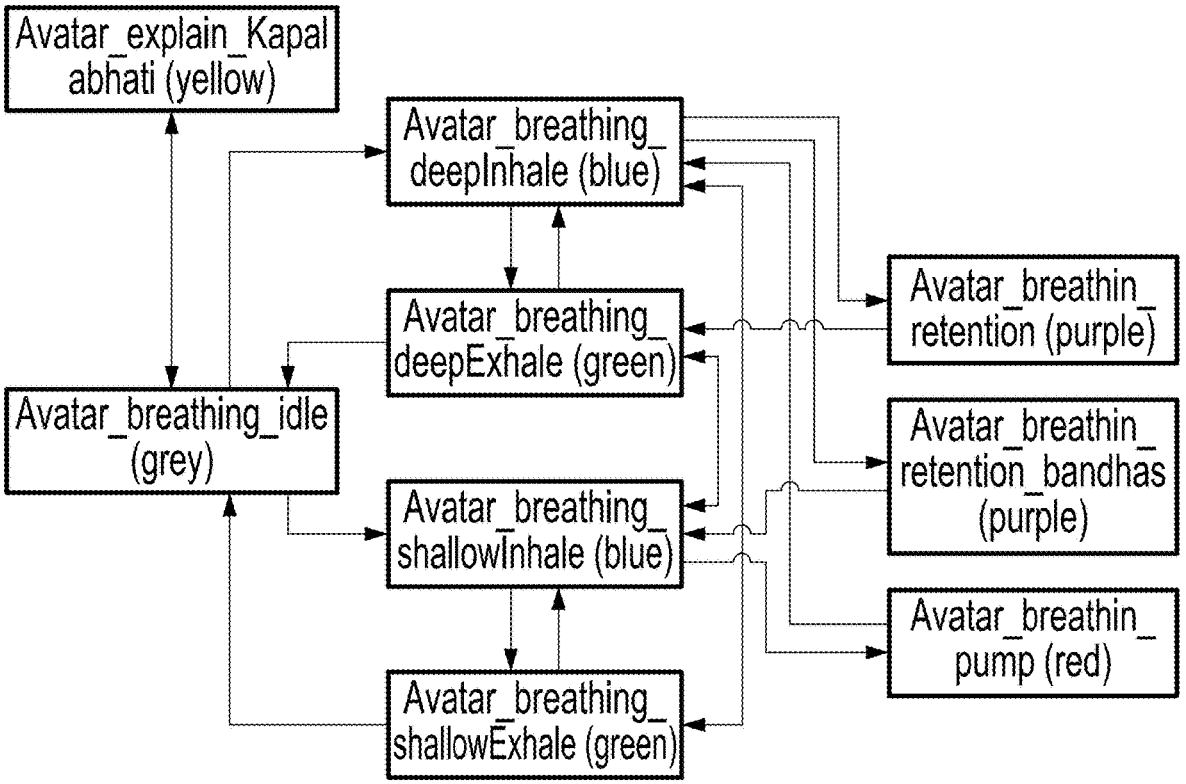
FIG. 1 is a schematic diagram illustrating statuses of a breath coach and their possible transitions, according to an embodiment.

The different required "states" of the breathing exercise are first defined. These states and their relationships form a graph of state possibilities, as illustrated in FIG. 1. As shown in FIG. 1, the "states" (each labelled box in the figure) relates to the animated status of the animated character to be displayed, but should also relate to the desired real-life breathing status of the person carrying out the breathing exercise. Accordingly, in terms of computer implementations, each state is used to define an animation, and the relationship threads together different states according to the exercise pattern.

The animation is performed by varying the body volume of a character, especially the thorax, according to the instructions (inhalation, exhalation, etc.), which are expected to have an effect on the volume of the upper body. An animated character can therefore be generated by computer and various visual states can be translated in a particular body appearance, with the transitions being also incorporated into the possible animations. At run time, the displayed animated character has an appearance which matches the exact action being instructed in the breathing exercise.

According to an exemplary embodiment, this pattern of actions, or sequence of consecutive instructions, is encoded in a pseudocode (flowchart of FIG. 2) which represents the actions to be performed by the computer, this flowchart acting as a template used to combine animation states as per variables given. This allows the automatic creation of multiple variations of this breathing exercise, by adjusting the variables, such as number of rounds, or how long the breath retention should be.

Figure 3:
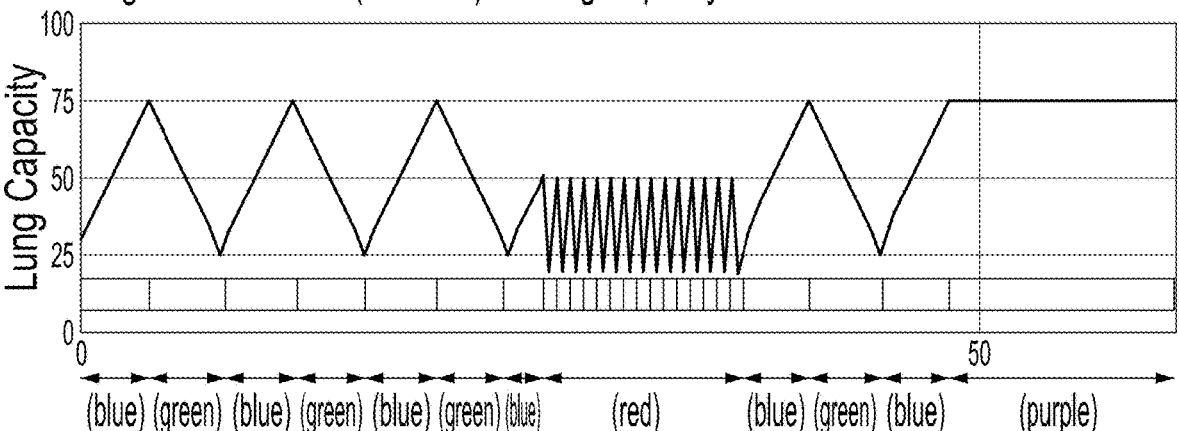
FIG. 3 is a graph illustrating lung capacity vs. time for different statuses of a breath coach and their possible transitions, according to an embodiment.
Figure 4:
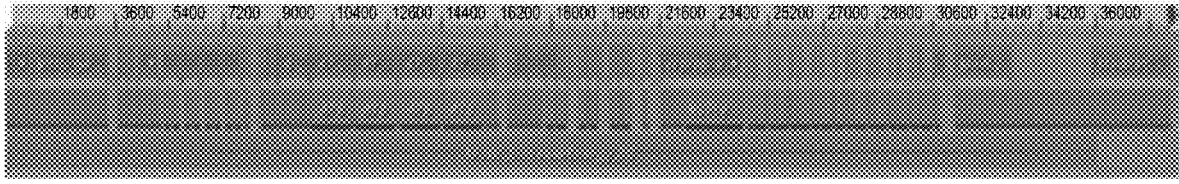
FIG. 4 is a schematic diagram illustrating a schematic timeline of breath events to be instructed in a given breath exercise, according to an embodiment.

Moreover, still according to an embodiment, an algorithm creates a timeline of a defined variation of a breathing exercise, which is a combination of audio recordings of instructions, the animations as defined by the computer internal representation of the status (FIG. 1), and the background music. An example of this timeline is illustrated in FIG. 4. Finally, as this timeline is played, a breathing pattern graph is produced, driven by the animation states, as illustrated in FIG. 3. In FIG. 3, the colored boxes match the colored boxes in FIG. 1, so for an example, during Avatar_breathing_deepInhale, a deep inhalation is shown in the graph (dark blue).

Figure 5:
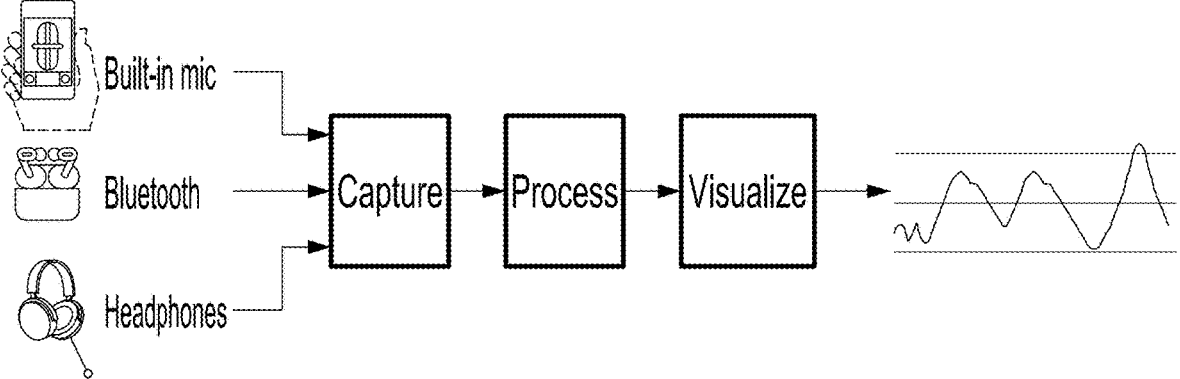
FIG. 5 is a schematic diagram illustrating data input, transformation and graphical output, according to an embodiment.

The data pipeline for live biofeedback analysis is illustrated in FIG. 5. First, the breath data is captured via an audio-detecting microphone which the user carries with him or her, or which is in the vicinity of the user with a sound detection range sufficient to detect the breath of this user, such as any one of the following: 1) Built-in microphone in any portable electronic device (e.g., any smartphone having iOS™, Android™, etc. installed thereon), 2) Bluetooth™ headphones with built-in microphone for any device (e.g., adapted for use by pairing with a smartphone, laptop, etc.), or 3) Headphones with a protruding microphone for any device (e.g., for a smartphone, phone system, laptop, gaming console . . . ).

Thus, the system is device-agnostic, and can be adapted to any platform. After data acquisition using any of the preceding type of microphone, the breath data is processed with signal-processing algorithms, and optionally visualized on a device of choice (the visualization being shown here to illustrate the underlying method of detection of breath).

Figure 6:
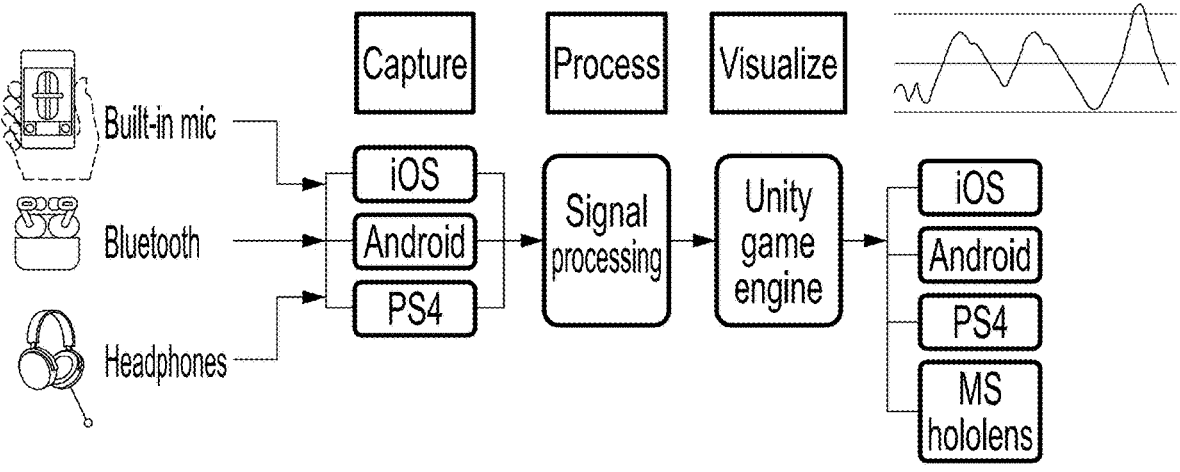
FIG. 6 is a schematic diagram illustrating data input, transformation and graphical output, including details of signal processing and graphical production, according to an embodiment.

An overview of the devices that an be used to implement the method is illustrated in FIG. 6. A platform-specific bridge is built for a specific device-type or brand (such as iOS™, Android™, PS4™, Xbox™, etc.) in order to capture the raw audio data which should contain the sound of breath.

A particular issue that needs to be addressed is that microphones or devices comprising a microphone typically filter out the sound of breath to improved sound quality, and that raw audio data is not typically available for use. Indeed, most of the time, when recording audio, the devices have built-in pre-processing functionalities to remove the background noise and improve the quality of the audio. This pre-processing however also removes the faint signal of the breath. The sound data which is required in the present method is therefore made inaccessible by the operating system which filters out useful raw data. This is especially problematic when using a game engine, such as Unity, by which dynamical applications may be implemented in practice, since when using such tools of development, there is a technical challenge regarding recording the breathing because the specific headphones cannot be selected as the device to use for audio capture, and the recording library of functions of such development tools does not allow any configuration. More specifically, the OS automatically does noise processing, which is a problem since this also may remove any breathing signal.

Thus, in order to capture the breath recordings, there is a need for the method to go past the pre-processing functions, i.e., to circumvent the pre-processing functions by using device-specific functionality to collect the raw data directly instead. According to an embodiment, a solution is to build a bridge where the game engine relies on code closer to the hardware, and to which device-specific and/or OS-specific instructions can be given to specifically start, process and output the raw data, thus having full control of the data processing. In the iOS example, this means writing native iOS code to leverage the native audio framework "Core Audio AV Foundation" to configure the audio capture settings to bypass automatic audio processing. The platform-specific code is written once per platform (OS-specific instructions) to address its audio recording specific configurations.

The raw data stream from the audio device can be accessed by using OS-specific instructions which allow accessing directly the raw audio file without the normal, default pre-processing performed automatically by the operating system (OS). Indeed, as mentioned above, it is the OS of the device which filters out noise from the built-in microphone of the device. Each OS should comprise instructions which, when performed by an application installed on the electronic device, allow retrieving the original data stream from the microphone on the device. For example, on an iPhone™, there are instructions which can be implemented in an installed application which instruct the operating system (iOS) to retrieve the raw audio stream of the iPhone's microphone instead of retrieving the typical OS-preprocessed audio stream. Equivalent methods can be applicable to other devices. In the case of external devices, such as Bluetooth-enabled microphones to be paired with the main electronic device, instructions should be found in the SDK (software development kit) to arrive at a similar result of retrieving the raw audio data stream instead of the pre-processed (noise-filtered) one.

Once this raw audio data stream is obtained, it is assumed that the so-called "noise" comprises sound from the breath, typically filtered out. Furthermore, this raw data is processed with signal processing algorithms according to the invention, which can be implemented, for example, and without limitation, in C#/C++/Matlab™. These algorithms can be applied to raw data received from any device.

According to an embodiment, and as shown in FIG. 6, at the next step, a game engine, such as Unity™ game engine, receives the data necessary to visualize the users breathing patterns, for example by plotting a graph. This breath pattern graph can be visualized on any device, such as on: 1) A smart phone (e.g., iOS™, Android™, etc.), 2) A game console (e.g., Xbox™, PS4™, etc.), or 3) AR/VR device (e.g., MS Hololens™, etc.).

The game engine is not required to produce a graph, although it is easier to use the game engine for this purpose if the graph is to be generated within the application itself. However, the game engine may prove additionally useful if the animated character of the displayed virtual coach (which gives oral instructions through the speaker of the electronic device) is adapted in real time to the measured feedback from the user. Whether the animated character depends from feedback from the user or not, the animated character is animated according to the expected pattern of breathing intensity in timing with the instructions, and displayed on the computing device.

In order to be able to measure the breath pattern in a useful manner, there needs to be a step of data acquisition with respect to the breathing of the user. According to an embodiment, from a microphone of any suitable electronic device in proximity to the user, the following information is captured with exemplary acquisition parameters.

First, the microphone is operated to record raw sound data, with the step of providing access to the raw sound data stream, as mentioned above, to avoid using the OS-preprocessed noise-filtered data stream. According to an embodiment, a sample window is used, every sample window being 100 ms long, the sound recording being performed at a sampling frequency of 16 000 Hz encoded in 16 bits. The 16-bit data are then converted to doubles (1600 doubles per window), and if file saving is to be used, this data is saved into a WAVE file. The whole file is then converted to an array of doubles.

As mentioned above, once recorded, the raw sound data stream can be split into sample windows of a duration comprised between 20 ms and 300 ms, preferably between 50 ms and 200 ms, more preferably between 80 ms and 120 ms, for example 100 ms. Once the raw sound data stream is split in a plurality of consecutive and distinct sample windows of this duration, each window can be analyzed independently by applying a method of detection of breath thereto.

In the case of a live version of analysis, the method of detection of breath is applied directly to each consecutive 100 ms-window at run time, in real time as the sound is recorded, without first saving it into a file (the saving into the file of the raw sound stream being therefore only necessary if the breath patterns are to be detected after the recording session).

In order to apply a method of detection of breath to the raw sound stream, the processor of the computer will execute instructions which cause it to detect features in the raw sound stream using detection parameters such as the following ones.

First, a moving averaging time window is applied on the consecutive sample windows to determine an average sound level. The deviation of the sound intensity compared to the average sound level, above or below a threshold, is used to determine if the sound includes breathing sound or not. This "threshold averaging time window" is set at a time duration between 0.8 s and 3 s, preferably between 1 s and 2 s, and more preferably at about 1.5 s.

FIG. 8 also shows the raw sound data stream, the stream transformed into IMF, and then the IMF envelope compared to the moving threshold, with breathing events detected in both graphs.

FIG. 9 illustrates, in the form of a pseudocode flowchart, the steps that are performed for transforming the data, detecting an intersection, and ensuring that the behavior of the standard deviation is indicative of the start of the breath event (or the end thereof), where the start of each breath event is time-stamped and recorded.

The parameters for the method for detecting breath in a raw data stream (previously formatted as mentioned above) can be fine-tuned with the parameters listed in Table 1.

TABLE 1

| Parameters used for breath detection (exemplary values) | |
| --- | --- |
| Parameter | Description |
| StandardDevRollingAvgFilterSmoothS | Moving average applied over the blue line (and teal line), typically 0.2 s. It helps removing undesirable noise spikes not related to breath. |
| DetectionThreadholdSmoothS | 1.5 s red line average filter is applied. Increasing this time will delay algorithm reactivity and increase CPU usage. |
| DetectionThreadholdMultiplier | Example value: 0.5. Variance is multiplied by this parameter as trigger input data (red line) |
| BreathDetectionMinHeightThreadholdFactor | How much should we go higher than the trigger line? |
| BreathDetectionMinWidthThreadholdS | Minimum time length to be considered breath |
| BreathDetectionMaxWidthThreadholdS | Maximum time of a breath |

A threshold multiplier, between 0.2 and 0.8, preferably between 0.4 and 0.6, preferably set at about 0.5, is used to determine how many times the standard deviation of the signal is representative of the threshold for detecting a breath event in the algorithm for breath detection, e.g., the threshold is stddev*0.5. The Breath Detection Threshold Factor represents how high stddev should be relative to moving threshold). There can be set a Breath Detection Minimum Time and a Breath Detection Maximum Time S.

The data captured is visually represented in FIG. 7, with the following color encoding: Purple: Represents the RAW audio signal; Red: Threshold, based on standard deviation with an offset and filtering with moving average on 1.5 s; Teal: Standard deviation calculated from IMF (explained below); Blue: Standard deviation shifted on X axis to match threshold and compensate lag.

In summary, first an EMD (Empirical Mode Decomposition) function is applied to the formatted raw sound data decompose the signal into a number of IMFs (Intrinsic Mode Functions). IMF is an oscillatory function with time-varying frequencies that represent the local characteristics of non-stationary signals. Then, for each sample, the average standard deviation is calculated (with reference to the algorithm below) along with the threshold value. Based on the difference between these two values, each intersection between a signal is detected by the processor. If the intersection is detected and the standard deviation is positive, a breath is detected, otherwise, it is not considered to be a breath event.

The audio signal is analyzed using the signal amplitude, which is typically measured in decibels. The dynamic threshold (red line below) is used to ignore the background noise from the process. This threshold adjusts itself continuously according to a moving averaging window of a duration of 1.5 seconds (this moving averaging window is configurable within the parameters mentioned above) so if the background noise increases, the red line will also increase on the graph shown in FIG. 7.

The algorithm expects to get as the input a MONO/DOUBLE 8 bytes-based audio signal. Typically, it is bounded $-1$ to $+1$. According to an embodiment, and depending on the implementation, it can be important to ensure it is a mono stream, as the algorithm may not be able to decode a stereo stream.

If this input type is not detected, a conversion is done before entering the algorithm. For example, let us suppose a 16,000 Hz sampling rate is used, and a data stream is delivered/inputted to the detection algorithm every 100 ms (duration of the sample window), so 1,600 double values are inputted per second. The algorithm can work well at other sampling frequencies, such as 8,000 Hz.

As the output of the detection algorithm, when the algorithm detects new breathing event, it will add it to a list (with a time stamp). Such events are then retrieved or accessed using these functions:

public IEnumerable<Breath>popBreathingDetections( )
  public IEnumerable<Breath>peekBreathingDetections( )

Breath object contains a flag indicating if detection is valid or why it was rejected if it's not valid. It also contains a timestamp. The "pop" variant will remove breathing from the list after being called, and "peek" will return breathing but without removing them from the list.

Figure 10:
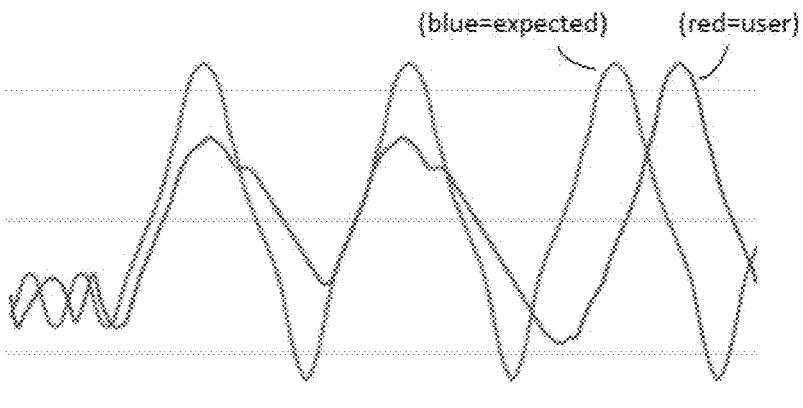
FIG. 10 is a graph illustrating an envelope of IMF of a user, as measured, compared to an ideal benchmark, according to an embodiment.

According to an embodiment, the breathing intensity is not only detected, but also its intensity is monitored and compared with the expected ideal breathing intensity pattern, as illustrated in FIG. 10, where this comparison with a benchmark can be shown to the user either in real time or a posteriori on the electronic device.

In order to collect good quality data and reduce background noise, it is important that the user is guided to be in a suitable environment for the breathing session. Before the breathing session begins, the user will be advised to be in a quiet room by themselves, and either wear headphones or have the phone within a maximum distance (range) from the mouth. According to an embodiment, this is followed by a calibration step, where the user is asked to take 3 normal breaths, allowing the system to calibrate the breathing exercise data against this 'normal' data, as shown in FIG. 10. The blue line is the coach's breathing pattern (the model pattern for the user to strive towards), and the red line is the user's actual (measured) breathing pattern, including intensity over a continuous period of time covering the exercise. In the case of FIG. 10, the same game engine as the one used to animate the character is used for displaying a plot of the formatted sound intensity (based on the IMF envelope, for example) in comparison with the expected pattern of breathing intensity over the continuous period of time (either simultaneously with the animated character or at an end of presentation of the animated character).

The blue line is a function of the coach's inhalations and exhalations, reacting to the body and lung movements of the animation, i.e., consistent with the breathing status, the expected associated breath events and timing as shown in the examples of FIGS. 1-3. The red line is the user's actual breathing, plotted from the output of the signal processing algorithm described above.

According to an embodiment, the lung movement, i.e., the lung volume or capacity over time and/or, equivalently, the volumetric flow of air which is expired/inspired over time, can be evaluated using the present method. In the case of nasal breathing, the base assumption of this evaluation is that the pulmonary flow (air flow) is proportional to the sound amplitude caused by the flow of air through the nostrils. It was found that this is not the case with the flow of air through the mouth, the sound of which can be modulated according to the shape given to the mouth. Also, interestingly, it was found that the audio spectrum of the sound produced by the nostrils during the passage of air can be characterized according to the flow rate, either by a displacement of the dominant frequency or the line appearance for certain air flow rates.

Figure 11:
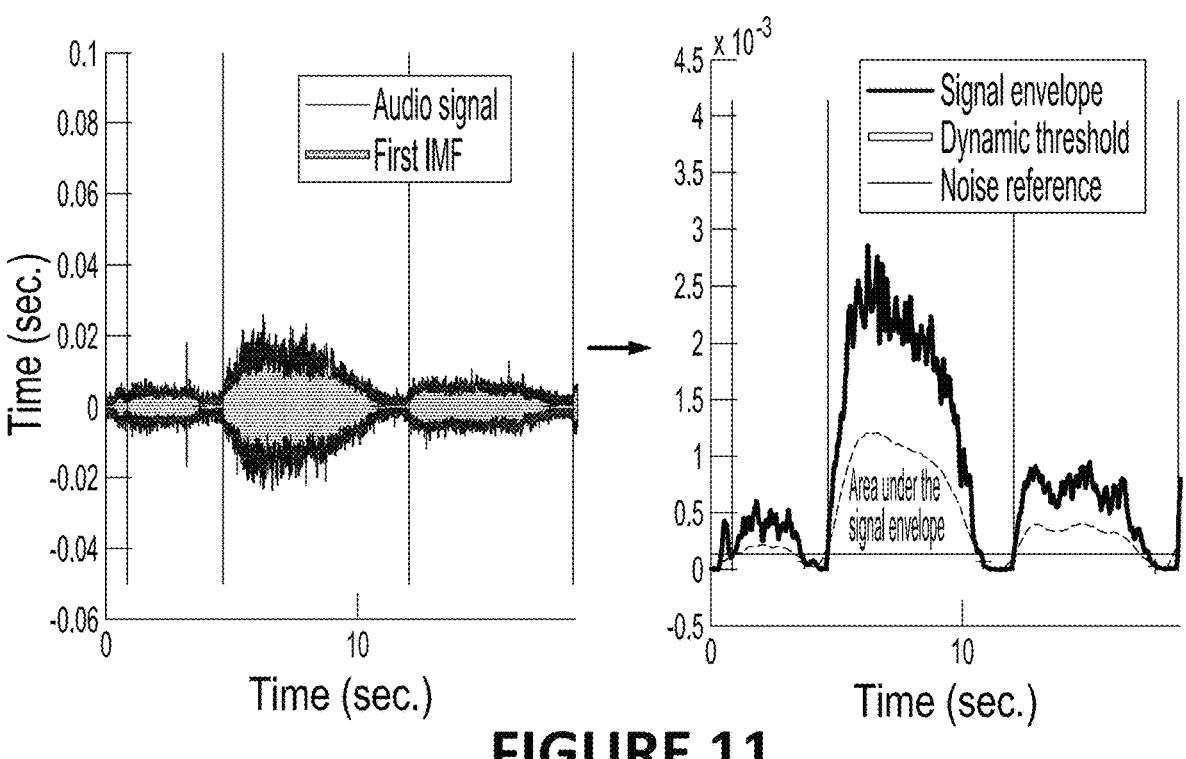
FIG. 11 is a pair of graphs illustrating a raw signal and its corresponding envelope of IMF of a user, as measured, which is integrated to evaluate volumetric air flow from and into the lungs, according to an embodiment.

Following the base assumption, if the amplitude of the sound signal produced by the breath during nasal breathing is proportional to its flow, the integration of the envelope of the signal (area under the curve) should be proportional to the volume of air inhaled or exhaled during a given time. The integration limits correspond to the beginning and the end of each inspiration and expiration. FIG. 11 is a pair of graphs illustrating a raw signal and its corresponding envelope of IMF of a user, as measured, which is integrated to evaluate volumetric air flow from and into the lungs over a period of time corresponding to the duration of a breath event (expiration or inspiration), resulting in the volume expired or inspired during an expiration or an inspiration, respectively, as mentioned above.

According to an embodiment, a calibration is carried out in order to determine for each user the relationship between the sound level and the air flow. The relationship between noise level and air flow may depend on several other factors that are determined and taken into account for each user. The calibration is based on the maximum lung capacity, i.e. one inspiration and a maximum expiration carried out as quickly as possible, and another over a longer period (4 to 5 sec.). Both measures should, in principle, give the same inspired and expired volume and help correlate the two.

According to an embodiment, there is further generated a session score to assess the quality of the data. The session score can be used to quantify the quality of the breathing session, representing how closely the user followed the coach. For example, scores can be calculated as follows:

$$sessionScore=(rhythmScore+amplitudeScore)*threshold Factor$$

$$rhythmScore=(\#peaks+\#troughs\ of\ user)/(\#peaks+\#troughs\ of\ model)-avg(distance\ between\ the\ overlaps)$$

$$amplitudeScore=sum(diff(peaks)+diff(troughs))$$

Through the mobile user interface, a personalized user experience is then offered to each individual user, based on their own respective preferences. First, a questionnaire may be implemented which asks why they want to practice breathing exercises and/or what objective they want to achieve. Then, the user is asked if they have certain medical conditions that would restrict them to perform the more challenging exercises. Finally, their current experience with breathing exercises is queried.

Based on the answers to the questionnaire, a personalized program is automatically generated for them, according to the restrictions, goals and previous experience, knowing that particular exercise programs are associated with a certain level of difficulty and a level of required physical engagement.

Further, as the user practices the exercises over a certain period of time (i.e., a plurality of exercises having been completed and assessed), the program can be automatically based on their past performance. If they are doing exceptionally well, a more challenging program is recommended. If they are underperforming, a more suitable program (i.e., lower level of difficulty) is recommended for the next exercise. The underlying logic is built to adapt to the user's current state, and to offer them exercises that help them grow and reach their objectives.

Figure 12:
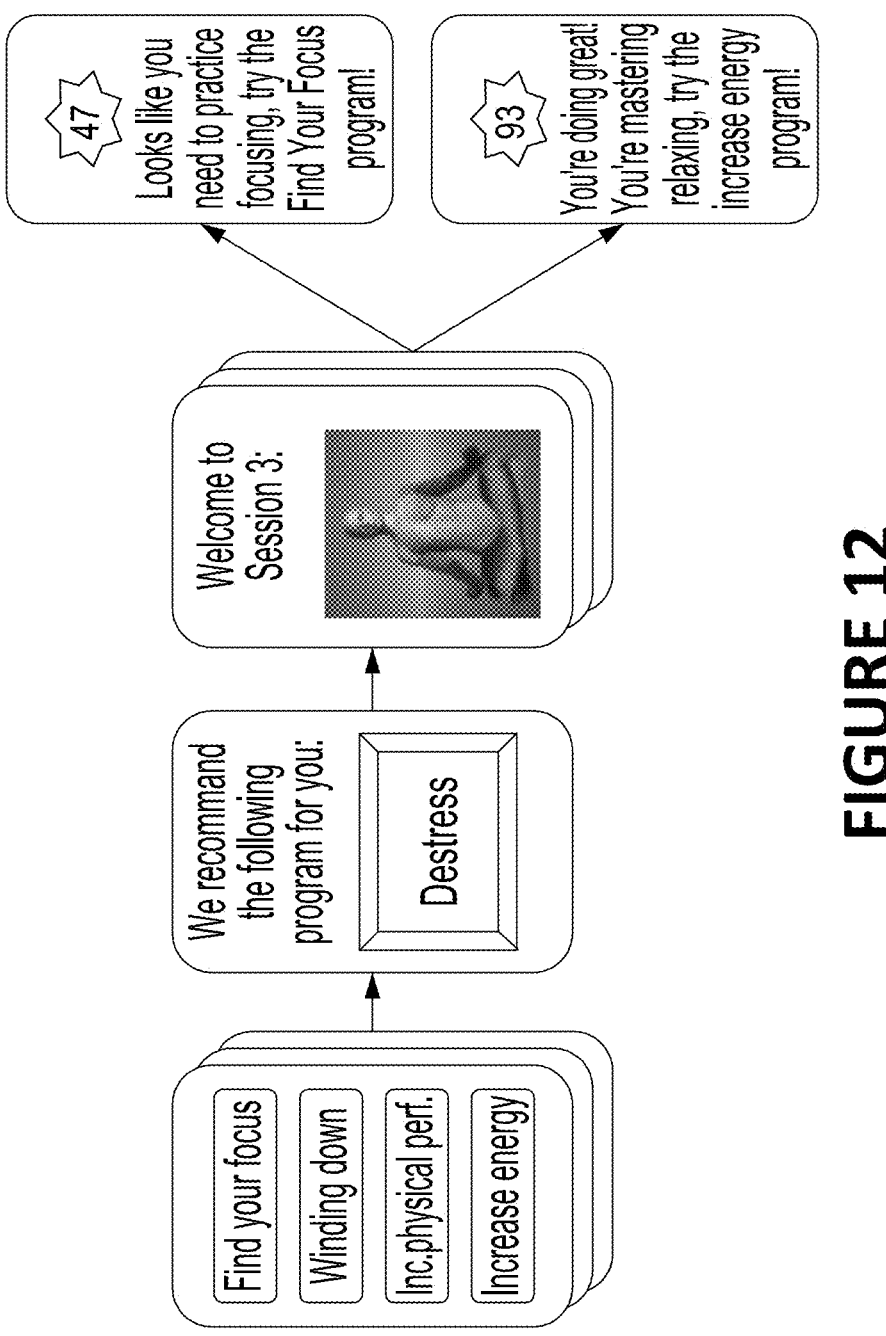
FIG. 12 is a schematic diagram illustrating a user interface for selecting a type of breath exercise, displaying an animated character and displaying a score indicative of the compliance of the user with the instructions, according to an embodiment.

A non-limiting example of a pathway that a user may follow is illustrated in FIG. 12. Throughout the onboarding process, as data about the user is collected, they select "Winding down" as their objective. Based on this information, the Destress program is recommended for them. They follow each session practicing the associated breathing exercises. After each session, the computer measures and showcases Session Score, determining how closely the user followed the coach's instructions. Finally, after 3 sessions, based on the Session Score, we adjust the recommendation, either to continue, try a program to practice a specific skill, such as focusing, or a more difficult program to challenge them further.

According to an embodiment, the output on the display of the user interface adapts to the live, real-time biofeedback. First, based on the user's initial profile settings, there is automatically recommended a breathing program to attain the desired objective, based on the user's experience level and medical restrictions. A breathing program is a sum of individual breathing sessions, where each session is a combination of 3 to 5 breathing exercises that the coach guides the user through.

Second, as the user starts to follow a session, the coach's instructions adapt to the user's performance, changing the length of the session according to the speed of the user's progress as measured using the breath detection algorithm and following score, evaluated dynamically in real-time during a session. The coach (i.e., the instructions being given to the user during the session) can automatically adapt the length of breath retentions, lengths of inhalations and exhalations as being measured during the session, and the number of repetitions of breathing exercises. For example, if a breathing exercise requires to hold the breath for 15 seconds 5 times, but they can only hold it for 10 seconds the first time, then the coach shall detect the breath events and evaluate the low score of compliance, where the low score of compliance as measured within the session indicates that the exercises are not well adapted to the level of the user, and therefore adapt the remaining 4 retentions to be 10 seconds long, for example, to be more adapted to the real-life level of the user as being measured in real-time.

Each day the user logs in, the coach can see where the user is that day, and adapt the length of retentions based their personal performance that day, to bring them to the final objective to complete the program.

Third, the overall objective of the breathing program is to improve the user's breathing quality and lung capacity, by incrementally giving more difficult exercises. For example, the next session has breath retentions for 5 seconds more than the previous one. The level of difficulty of the exercises is therefore adapted to be more in line with an actual level of the user within a session, and is gradually increased over successive sessions (i.e., during the program) to force the user to improve in the long term.

Figure 13:
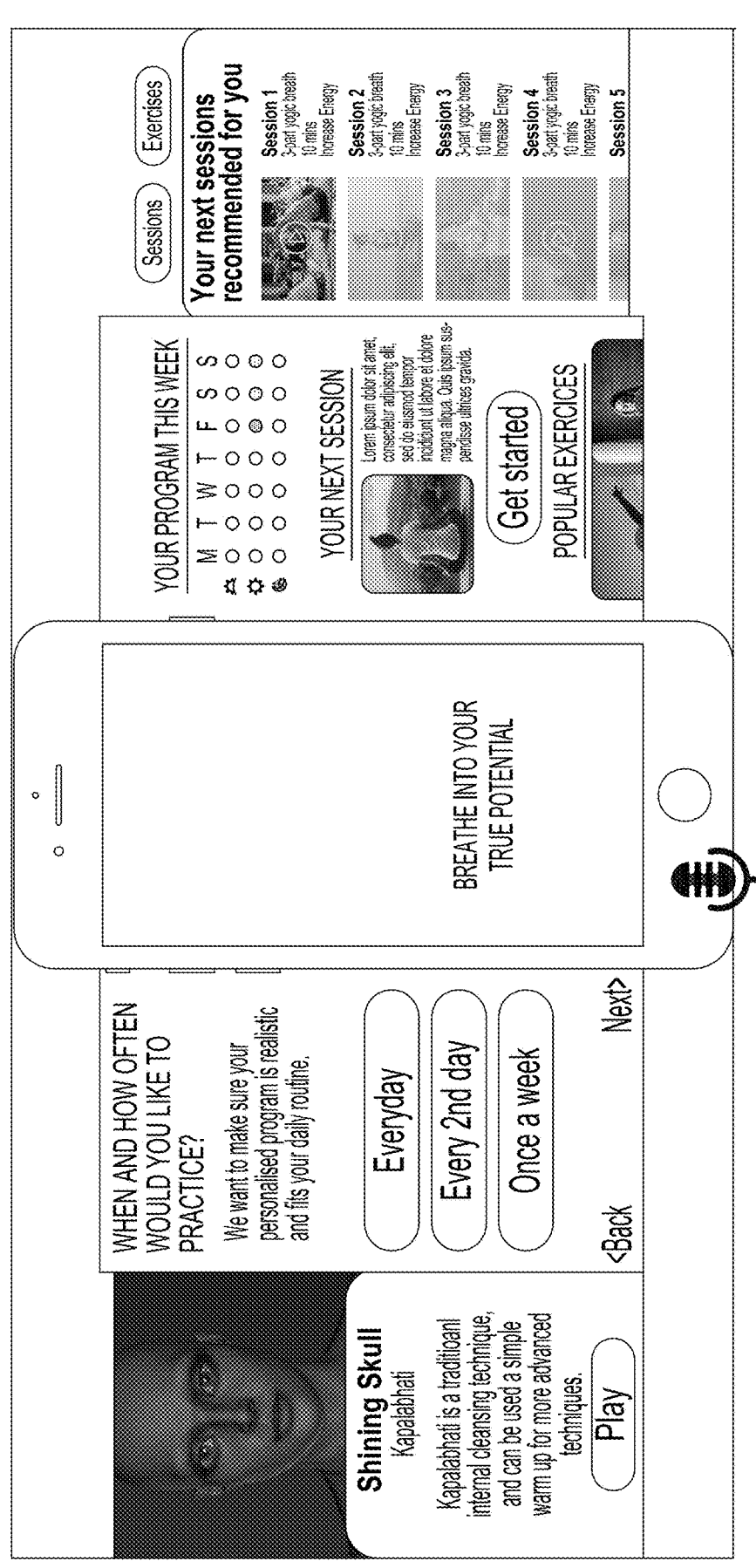
FIG. 13 is a schematic diagram illustrating an electronic device having a microphone and a display for displaying a graphical user interface which is tactile, with various possible interfaces for recommending and selecting a type of breath exercise, displaying an animated character and displaying a calendar with an exercise program, according to an embodiment.

FIG. 13 is a schematic diagram illustrating an electronic device having a microphone and a display for displaying a graphical user interface which is tactile, with various possible interfaces for recommending and selecting a type of breath exercise among an available library of exercises, displaying an animated character with a particular esthetics and displaying a calendar with an exercise program.

The method described above is advantageously implemented on a computing device, typically portable or handheld, such as a smartphone (as shown in FIG. 13, having a built-in microphone and an interactive display screen), a tablet, a phablet, or a web-enable device wearable device (watch, glasses, etc.). Most or all steps are executed locally, by the processor of the device which executes the instructions stored thereon (application installed thereon). Optionally, a few steps such as a posteriori analysis of the data can be performed on a remote server, in which case a web connection is required.

In all cases, the computing device is essential for carrying out the method, since the sound data needs to be collected in a quantifiable manner only available with computing devices, especially since transformed data sets are to be computed in real time. It follows that the microphone associated to the computing device (either associated permanently or temporarily) is also essential for carrying out the method.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A computer-implemented method for acquiring a raw audio data stream and detecting breathing events on a computing device, the method comprising:
providing a microphone, wherein the microphone is a built-in microphone integrated to the computing device, to collect the raw audio data stream;
providing an operating system installed on the computing device;
by the operating system, preprocessing the raw audio data stream collected by the microphone by default for access to the preprocessed raw audio data stream by any application installed on the computing device;
by the computing device, providing a sequence of user instructions for the breathing exercise;
determining an expected pattern of breathing intensity from the user in accordance with the sequence of user instructions;
retrieving the raw audio data stream collected by the microphone from the computing device, wherein the step of retrieving the raw audio data stream comprises:
using OS-specific instructions directed to the operating system to avoid receiving the preprocessed raw audio data stream and instead retrieving the raw audio data stream, not preprocessed, directly, by preventing any alteration by the operating system on the raw audio data stream before retrieval, and therefore different from the preprocessed raw audio data stream;
detecting breathing events from the raw audio data stream,
wherein the raw audio data stream is transformed into a formatted raw audio data stream by dividing the raw audio data stream in independently treated sample windows of a duration between 50 ms and 200 ms, converting the raw audio data stream from 16-bit to double and wherein the formatted raw audio data stream is transformed into a formatted sound intensity by decomposing the formatted raw audio data stream into Intrinsic Mode Functions using Empirical Mode Decomposition;
wherein the detecting comprises:
detecting that the formatted sound intensity has crossed over a threshold, wherein the threshold is based on a moving averaging window of the formatted sound intensity of a duration between 1 s and 2 s;
integrating the formatted sound intensity over a continuous period of time covering a detected breath event to evaluate a volume of air that was inspired or expired during the detected breath event; and
comparing the formatted sound intensity over a continuous period of time with the expected pattern of breathing intensity.

2. The method of claim 1, wherein detecting breathing events further comprises:
determining the threshold for each of the sample windows based on the moving averaging window and identifying intersections of the threshold with an envelope of the Intrinsic Mode Functions;
for each of the sample windows, calculating an average standard deviation and the threshold to discriminate between a start and an end of the detected breath event; and
recording and time-stamping each start of the detected breath event.

3. The method of claim 1, further comprising:
based on the comparing of the timing of the detected breathing events with the expected pattern of breathing intensity to determine compliance with the breathing exercise, generating a score indicative of the compliance; and
among a library of possible breathing exercises, automatically proposing a future breathing exercise with an adjusted level of difficulty which is based on a level of difficulty of the breathing exercise which was performed and on the score indicative of the compliance.

4. The method of claim 1, further comprising:
using a game engine, animating an animated character according to the expected pattern of breathing intensity in timing with the instructions, and displaying the character on the computing device.

5. The method of claim 1, further comprising:

adapting future instructions of the breathing exercise based on the step of comparing such that if the step of comparing indicates a low compliance with the expected pattern of breathing intensity, a level of difficulty of the future instructions is lowered within a single session of the breathing exercise.

6. The method of claim 1, further comprising:

using a game engine, animating an animated character according to the expected pattern of breathing intensity in timing with the instructions, and displaying the animated character on the computing device; and using the same game engine, displaying a plot of the formatted sound intensity in comparison with the expected pattern of breathing intensity over the continuous period of time simultaneously with the animated character or at an end of presentation of the animated character.

7. A computing device for acquiring a raw audio data stream and detecting breathing events, the computing device comprising a microphone, a memory storing instructions and a processor executing the instructions to execute steps of:

providing, on the computing device, a sequence of user instructions for the breathing exercise;

determining an expected pattern of breathing intensity from the user in accordance with the sequence of user instructions;

retrieving the raw audio data stream from the microphone;

detecting breathing events from the raw audio data stream, wherein the raw audio data stream is transformed into a formatted raw audio data stream by dividing the raw audio data stream in independently treated sample windows of a duration between 50 ms and 200 ms, converting the raw audio data stream from 16-bit to double and wherein the formatted raw audio data stream is transformed into a formatted sound intensity by decomposing the formatted raw audio data stream into Intrinsic Mode Functions using Empirical Mode Decomposition;

wherein the detecting comprises:

detecting that the formatted sound intensity has crossed over a threshold, wherein the threshold is based on a moving averaging window of the formatted sound intensity of a duration between 1s and 2s;

integrating the formatted sound intensity over a continuous period of time covering a detected breath event to evaluate a volume of air that was inspired or expired during the detected breath event; and comparing the formatted sound intensity over a continuous period of time with the expected pattern of breathing intensity, wherein the microphone is a built-in microphone integrated to the computing device, wherein the computing device comprises an operating system which preprocesses the raw audio data stream from the microphone by default for access to the preprocessed raw audio data stream by any application installed on the computing device, and wherein the step of retrieving the raw audio data stream comprises:

using OS-specific instructions directed to the operating system to avoid receiving the preprocessed raw audio data stream and retrieving the raw audio data stream, not preprocessed, directly, by preventing any alteration by the operating system on the raw audio data stream before retrieval.

8. The computing device of claim 7, wherein detecting breathing events comprises:

determining the threshold for each of the sample windows based on the moving averaging window and identifying intersections of the threshold with an envelope of the Intrinsic Mode Functions;

for each of the sample windows, calculating an average standard deviation and the threshold to discriminate between a start and an end of the detected breath event; and recording and time-stamping each start of the detected breath event.

9. The computing device of claim 7, further comprising:

based on the comparing of the timing of the detected breathing events with the expected pattern of breathing intensity to determine compliance with the breathing exercise, generating a score indicative of the compliance; and among a library of possible breathing exercises, automatically proposing a future breathing exercise with an adjusted level of difficulty which is based on a level of difficulty of the breathing exercise which was performed and on the score.

10. The computing device of claim 7, further comprising:

using a game engine, animating an animated character according to the expected pattern of breathing intensity in timing with the instructions, and displaying the animated character on the computing device; and using the same game engine, displaying a plot of the formatted sound intensity in comparison with the expected pattern of breathing intensity over the continuous period of time simultaneously with the animated character or at an end of presentation of the animated character.

11. A computer-implemented method for acquiring a raw audio data stream and detecting breathing events using a computing device, the method comprising:

providing a microphone which collects the raw audio data stream, wherein the microphone is a built-in microphone integrated to the computing device;

providing an associated logic module on the microphone, by the associated logic module on the microphone, preprocessing the raw audio data stream from the microphone by default for access to the preprocessed raw audio data stream by any application installed on the computing device;

by the computing device, providing a sequence of user instructions for the breathing exercise;

determining an expected pattern of breathing intensity from the user in accordance with the sequence of user instructions;

retrieving the raw audio data stream collected by the microphone from the computing device, wherein the step of retrieving the raw audio data stream comprises:

using instructions directed to the associated logic module of the microphone to avoid receiving the preprocessed raw audio data stream and instead retrieving the raw audio data stream, not preprocessed, directly, by preventing any alteration by the logic module of the microphone on the raw audio data stream before retrieval, and therefore different from the preprocessed raw audio data stream;

detecting breathing events from the raw audio data stream, wherein the raw audio data stream is transformed into a formatted raw audio data stream by dividing the raw audio data stream in independently treated sample windows of a duration between 50 ms and 200 ms, converting the raw audio data stream from 16-bit to double and wherein the formatted raw audio data stream is transformed into a formatted sound intensity by decomposing the formatted raw audio data stream into Intrinsic Mode Functions using Empirical Mode Decomposition;

wherein the detecting comprises:

detecting that the formatted sound intensity has crossed over a threshold, wherein the threshold is based on a moving averaging window of the formatted sound intensity of a duration between 1s and 2s;

integrating the formatted sound intensity over a continuous period of time covering a detected breath event to evaluate a volume of air that was inspired or expired during the detected breath event; and comparing the formatted sound intensity over a continuous period of time with the expected pattern of breathing intensity.

* * * * *